United States Patent [19]

Abraham

[11] Patent Number: 4,784,850

[45] Date of Patent: Nov. 15, 1988

[54] PROCESS FOR PREPARING ANTIBODIES AGAINST E. COLI K-99 ANTIGEN FROM BOVINE MILK

[75] Inventor: Gilead B. Abraham, Doar Maabarot, Israel

[73] Assignee: Mutzarei Maabarot, Israel

[21] Appl. No.: 772,399

[22] Filed: Sep. 4, 1985

[51] Int. Cl.$^4$ .................. A61K 39/40; C07K 15/06
[52] U.S. Cl. ........................ 424/87; 424/95; 530/387; 530/412; 530/414; 530/832
[58] Field of Search ............. 530/387, 412, 414, 832; 424/85, 87, 95

[56] References Cited

U.S. PATENT DOCUMENTS

| 4,443,547 | 4/1984 | Gouet et al. | 435/253 |
| 4,443,549 | 4/1984 | Sadowski | 436/548 |
| 4,652,448 | 3/1987 | Sadowski | 424/87 |

OTHER PUBLICATIONS

Trainin, Z. et al., Refuah Vet. 38(1-2) 1981, pp. 1-3.
Kornitzer, I. et al., Refuah Vet. 37(3):71-80 (1980).
Danieli, Y. et al., Refuah Vet. 36(4):125-130 (1979).
Sasaki, M. et al., Jap. J. Zootech, 42(4):180-190 (1971).

Primary Examiner—Margaret M. Moskowitz
Attorney, Agent, or Firm—Berman, Aisenberg & Platt

[57] ABSTRACT

The present invention relates to a process for the manufacture of a preparation containing specific antibodies against the K-99 antigen of various strains of enterotoxigenic *Escherichia coli* (etec). In said process the milk obtained from postpartum cows, which had been previously vaccinated with *E. coli* strain 168, is clotted with a suitable enzyme. The fatty serum is then separated from the cheese obtained, the fat is then separated out, the fat-free serum is then subjected to ultrafiltration through a suitable number of appropriate membranes so that 30-50% of the water present is removed the retentate is then sterilized. Suitable membranes are those which are permeable only to molecules of less than about 22,000-30,000 daltons molecular weight. The preparation is advantageously lyophilized and the lyophilized preparation is subsequently sterilized by irridation, e.g. with $Co^{60}$.

11 Claims, No Drawings

PROCESS FOR PREPARING ANTIBODIES AGAINST E. COLI K-99 ANTIGEN FROM BOVINE MILK

The present invention relates to a process for the manufacture of a preparation containing specific antibodies against the K-99 antigen of various strains of enterotoxigenic *Escherichia coli* (ETEC). (Hereinafter "the preparation").

The disease caused by the ETEC infection in newborn calves causes severe losses in many countries. The main factor in enabling ETEC infection to cause the disease is the K-99 antigen.

It has been established by Z. Trainin et al, Refuah Vet. 38 (1-2), 1981, that when the above preparation was orally administered to newborn calves which had been inoculated with massive doses of ETEC the mortality of the calves was 10% compared with 94% of non-immunized control calves.

Said preparations are prepared from milk obtained the first day post-partum of cows which had been previously vaccinated with *E. coli* strain 168. Certain production processes of same are known, for example, from Y. Danieli et al., Refuah Vet. 36, 125-130 (1979) and from I. Kornitzer et al., Refuah Vet. 37, 71-80 (1980). However, said known processes are not entirely satisfactory. Their main drawback is that the final preparation has not always the desired particle size and is thus either not easily soluble in water, making the product infeasibly inconvenient to use, or is made soluble by a process that is too expensive for the product to be economically feasible.

It was therefore desirable to devise a process which produces a preparation that has the desired efficacy and an extended storage life, is simple and convenient to use by the farmer and relatively simple and economic to manufacture.

It has been established that the desired efficacy of the preparation is an agglutination titre of 1:2500-3000 when one dose is dissolved in 10 ml of water, and that this efficacy can be obtained by the present invention described hereinafter.

The present invention thus consists of a process for the manufacture of a preparation (as herein defined) in which the milk obtained from postpartum cows, which had been previously vaccinated with *E. coli* strain 168, is clotted, the fatty serum is then separated from the cheese obtained, the fat in said serum is then separated out, the fat-free serum is then subjected to ultrafiltration through a suitable number of appropriate membranes so that 30-50% of the water present is removed and the retentate, being the desired preparation, is then sterilized.

The clotting step is advantageously performed in the course of 20-40 minutes at about 40°-50° C. with 500-1500 ml of diluted enzyme.

Any of the enzymes generally used for clotting milk may be utilized, e.g. "chicken pepsin preparation M-MCP-21" (made by Development and Production of Enzymes Co. Ltd., Israel). The rate of dilution is about 1 ml enzyme to 5-10 ml water for each 1000 ml of milk. However, the present invention is not restricted to this enzyme and to this rate of dilution.

The fatty serum is advantageously separated from the cheese by way of filtration, the serum being the filtrate. The residue of the fatty serum may be obtained by pressing the cheese remaining after the filtration step.

The fat may be separated by any suitable method, e.g. by centrifugation.

The ultrafiltration may be performed with any suitable membrane, permeable only to molecules of less than about 22,000-30,000 daltonsmolecular weight, which does not react with the serum suspension and does not have any toxic effect thereon. The number of membranes may be varied, e.g., from about 10-70, preferably 25-40. The larger the number of membranes the larger the quantity per minute of permeate. A suitable membrane is, for example, type GR, 61 pp of De Danske Sukkerfabrikker, Denmark.

The sterilization may be performed in any suitable manner. For example, the preparation may be pressed through a suitable membrane which filters out bacteria, or may be treated with a suitable sterilizing agent, e.g. formalin, phenol, etc. Naturally, said agent should not react with the preparation and not have any toxic effect thereon. Another suitable method is to subject the final preparation to irradiation, e.g. with $Co^{60}$. Sometimes more than one sterilization method will be utilized.

The final liquid preparation thus produced can be stored by deep-freezing. However, it is preferable to lyophilize the liquid preparation, thus producing a dry final product which can then be stored at room temperature. It is advantageous to subject the lyophilized preparation to irradiation.

Single doses, 10-15 ml of the final liquid preparation, are advantageously filled into small bottles of about 25 ml prior to lyophilization. A dose of the final dry preparation has the desired efficacy of an agglutination titre of 1:2500-3000 when dissolved in 10 ml of water. When the preparation is to be used, the farmer dissolves said dose in about 10-20 ml of water, mixes the solution obtained with about 250 ml of colostrum and then administers the mixture orally to the newborn calf.

The preparation obtained by the process according to the present invention dissolves within a few minutes, whereas preparations produced by previously known processes take 2-6 hours to dissolve completely.

The present invention will now be illustrated with reference to the following examples without being limited by same.

EXAMPLE a. Vaccination

The pregnant cows were vaccinated three times in intervals of 3 weeks during the last 9 weeks before calving, each time with 5 ml of absolutely inactivated *E. coli* strain 168. Thereafter the milk was collected the first day postpartum.

b. Clotting and separation of fatty serum

The clotting of 4 different batches and the fatty serum was separated as shown in Table I.

TABLE 1

| Batch | 1 | 2 | 3 | 4 |
|---|---|---|---|---|
| Amount of milk (Liters) | 128 | 93 | 90 | 77 |
| Temperature of milk before heating (°C.) | 6 | 10 | 11 | 6 |
| Duration of heating (minutes) | 25 | 20 | 22 | 25 |
| Temperature of milk after heating (°C.) | 43 | 42 | 44 | 45 |
| Quantity of diluted enzyme (ml) | 1000 | 850 | 750 | 500 |
| Rate of clotting (minutes) | 2 | 3 | 2 | 1.5 |
| Duration of mixing (minutes) | 3 | 4 | 3.5 | 2 |
| Waiting period (minutes) | 25 | 35 | 18 | 30 |
| Quantity of cheese collected (kg) | 28 | 21 | 20 | 12.75 |

TABLE 1-continued

| Batch | 1 | 2 | 3 | 4 |
|---|---|---|---|---|
| Quantity of cheese after pressing (kg) | 26 | 16 | 16 | 10.75 |
| Quantity of total fatty serum obtained | 102 | 77 | 74 | 66.25 |

The enzyme used was chicken pepsin M-MCP-21. The rate of dilution in water was 1:9. (for each 1000 ml of milk)

c. Separation of fat

Fat was separated out from the fatty serum obtained by centrifugation and the results are given in Table II.

TABLE II

| Batch | 1 | 2 | 3 | 4 |
|---|---|---|---|---|
| Temperature of serum before first separation (°C.) | 38 | 40 | 39 | 40 |
| Quantity of fat removed by first separation (kg) | 7.2 | 5 | 4 | 3 |
| Temperature of serum before second separation (°C.) | 33 | 35 | 33 | 35 |
| Quantity of fat removed by second separation (kg) | 0.8 | 0.5 | 0.5 | 1 | d. Ultrafiltration

The conditions under which the ultrafiltration was performed and the results thereof are illustrated in Table III. The ultrafiltration was performed with various batches collected from the previous steps. These batches are thus indicated as 1', 2', 3' and 4', respectively.

TABLE III

| Batch | 1' | 2' | 3' | 4' |
|---|---|---|---|---|
| Number of membranes | 35 | 27 | | 38 |
| Production parameters: | | | | |
| Pressure (pressure gauge II) (atm) | 2 | 2.5 | 3 | 2.8 |
| Variator | 8 | 6 | 7.5 | 8 |
| Temperature of tap water (°C.) | 20 | 22 | 21 | 22 |
| Permeate output (l/minute) | 0.5 | 0.7 | 1 | 1 |
| Retentate output (l/minute) | 7 | 5.8 | 6 | 6.5 |
| Quantity of serum before filtration (l) | 94 | 71.5 | 69.5 | 62.25 |
| Temperature of serum (°C.) | 30 | 32 | 29 | 31 |
| Input pressure (atm) (end process) | 27 | 26 | 30 | 25 |
| Retentate temperature (°C.) | 35 | 40 | 45 | 38 |
| Duration of filtration (minutes/10 l) | 35 | 30 | 32 | 28 |
| Retentate (l) | 47 | 39 | 35 | 34.5 |
| Permeate (l) | 42 | 29 | 27 | 24.5 |

The difference between the volume of serum and the sum of the volumes of the retentate and permeate is due to differences in specific weights.

The membrane used was the above mentioned type GR, 61 pp.

e. Sterilisation

The retentates obtained in step "d" were each sterilized by a 10% v/v solution of formalin in sterile water. The conditions are shown in Table IV

TABLE IV

| Batch | 1' | 2' | 3' | 4' |
|---|---|---|---|---|
| Sterilization temperature (°C.) | 37 | 39 | 38 | 37 |
| Quantity of diluted formalin (ml) | 470 | 390 | 350 | 345 |
| Sterilization time (hours) | 2 | 2 | 2 | 2 |
| Duration of storage at 5° C. | 24 | 24 | 24 | 24 |

The agglutination titre of the preparation obtained (when one dose was dissolved in 10 ml water) was 1:2500-3000.

f. Lyophilization and irradiation

Each of the above preparations was subjected to lyophilization.

The small bottles of liquid preparation were cooled to −45° C. and then, under vacuum of 20 microns Hg, heated to 30°-35° C., sublimating to a moisture content of 2-3%. The bottles were then hermetically sealed and irradiated with 2.0-3.0 megarad from Cobalt[60].

The final preparations were tested by the Laboratory of Vaccine Control of the Israeli Ministry of Agriculture, Veterinary Services & Animal Health. The following results were achieved:

| Agglutination titer | 1:256 (when 1 dose was dissolved in 120 ml of water) |
|---|---|
| Sterile | (+) |
| Toxic for mice | (−) |

The preparations can be stored for 2 years. When the preparation is to be used, the bottle is opened and the contents are dissolved in 10 ml of sterile water in the course of few minutes, then admixed with 250 ml of colostrum and finally administered to the newborn calf.

I claim:

1. A process for manufacturing a preparation containing antibodies which specifically bind to the K-99 antigen of strains of enterotoxigenic *Escherichia coli* which comprises:
   clotting milk obtained from a postpartum cow, which had been previously vaccinated with *E. coli* strain 168,
   separating fatty serum from cheese obtained therefrom,
   separating out fat from said fatty serum,
   subjecting resulting fat-free serum to ultrafiltration to remove from 30 to 50% of water present, and
   sterilizing the resulting retentate.

2. A process according to claim 1 wherein the clotting is performed with chicken pepsin preparation M-MCP-21 in a dilution of 1 ml of enzyme to from 5 to 10 ml of water for each 1000 ml of milk.

3. A process according to claim 1 wherein the ultrafiltration is effected through at least one membrane which is permeable only to molecules of less than about 22,000 to 30,000 daltons molecular weight.

4. A process according to claim 3 wherein the ultrafiltration is effected through at least one membrane which is type GR 61 pp.

5. A process according to claim 3 wherein the ultrafiltration is effected through from 10 to 70 membranes.

6. A process according to claim 3 wherein the ultrafiltration is effected through from 25 to 40 membranes.

7. A process according to claim 1 wherein the sterilizing is performed with formalin.

8. A process according to claim 1 wherein the sterilizing is performed by irrdiation.

9. A process according to claim 1 which comprises lyophilizing the sterilized retentate.

10. A process according to claim 9 which comprises sterilizing the resulting lyophilizate by irradiation.

11. A process according to claim 9 which comprises sterilizing the resulting lyophilizate by irradiation with $Co^{60}$.

* * * * *